United States Patent

Cook et al.

[11] Patent Number: 5,185,375
[45] Date of Patent: Feb. 9, 1993

[54] THIOFORMAMIDE DERIVATIVES

[75] Inventors: David C. Cook, London; Terance W. Hart, Brentwood; Iain M. McLay, Coughton; Malcolm N. Palfreyman, Upminster; Roger J. A. Walsh, Rayleigh, all of England

[73] Assignee: May & Baker Limited, Dagenham, England

[21] Appl. No.: 503,119

[22] Filed: Mar. 30, 1990

Related U.S. Application Data

[63] Continuation of Ser. No. 285,114, Dec. 16, 1988, abandoned.

[30] Foreign Application Priority Data

Dec. 18, 1987 [GB] United Kingdom ............... 8729522

[51] Int. Cl.$^5$ ................ A61K 31/16; C07C 327/00
[52] U.S. Cl. .................... 514/599; 514/332; 514/357; 514/522; 514/524; 514/535; 514/542; 514/562; 514/590; 514/826; 514/927; 546/265; 546/267; 546/286; 546/287; 558/412; 558/422; 560/9; 562/426; 564/34; 564/74; 564/251
[58] Field of Search ............... 564/74; 514/599, 522, 514/524, 535, 542, 562, 826, 927; 558/412, 422; 560/9; 562/426

[56] References Cited

U.S. PATENT DOCUMENTS 3,576,862  4/1971  Chupp .................... 564/74

FOREIGN PATENT DOCUMENTS 1466416  1/1967  France .................... 564/74
0566811  12/1974  Switzerland ............ 564/74

Primary Examiner—Richard L. Raymond
Assistant Examiner—P. O'Sullivan
Attorney, Agent, or Firm—Morgan & Finnegan

[57] ABSTRACT

Therapeutically useful thioformamide derivatives of the formula:

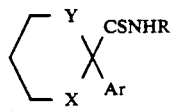

wherein R represents alkyl, Ar represents optionally substituted phenyl group, Y represents ethylene, methylene or a valency bond, and X represents carbonyl, hydroxymethylene, $>C=NOR^1$, $>C=NN(R^1)_2$ or $>C=NN(R^1)CON(R^1)_2$ in which $R^1$ represents hydrogen or optionally substituted alkyl, benzyl, phenethyl, 1-naphthylmethyl, 2-naphthylmethyl or pyrid-3-ylmethyl or two $R^1$ substituents on the same nitrogen atom may together form optionally substituted alkylene, and salts thereof, processes for their preparation and compositions containing them are described.

8 Claims, No Drawings

THIOFORMAMIDE DERIVATIVES

This application is a continuation of application Ser. No. 285,114, filed Dec. 16, 1988, now abandoned.

This invention relates to new therapeutically useful thioformamide derivatives, to processes for their preparation and to pharmaceutical compositions containing them.

The new thioformamide derivatives of the present invention are those compounds of the general formula (I) hereinafter depicted, wherein R represents a straight- or branched-chain alkyl radical containing from 1 to 4 carbon atoms, Ar represents an optionally substituted phenyl group, Y represents a valency bond or an ethylene or preferably methylene radical, and X represents a carbonyl or hydroxymethylene group or a group of the formula: $>C=NOR^1$, $>C=NN(R^1)_2$ or $>C=NN(R^1)CON(R^1)_2$ in which the symbols $R^1$, which may be the same or different, each represents the hydrogen atom or a straight- or branched-chain alkyl radical containing from 1 to 4 carbon atoms which is unsubstituted or substituted by one or more substituents selected from $C_{2-4}$-alkenyl, carboxy, $C_{2-5}$-alkoxycarbonyl, hydroxy, $C_{1-4}$-alkoxy, carbamoyl (unsubstituted or substituted by one or two $C_{1-4}$-alkyl groups), amino, $C_{1-4}$-alkylamino and di-$C_{1-4}$-alkylamino groups (e.g. $R^1$ may represent a methyl, 2-hydroxy-3-isopropyl-aminopropyl or 2-hydroxy-3-t.butylaminopropyl radical), or represents a benzyl, phenethyl, 1-naphthylmethyl, 2-naphthylmethyl or pyrid-3-ylmethyl radical each of which may be substituted on the ring by one or more halogen atoms or hydroxy, $C_{1-4}$-alkyl, $C_{1-4}$-alkoxy (alkoxy being unsubstituted or substituted as defined for alkyl groups represented by $R^1$), cyano, nitro, trifluoromethyl, carboxy, $C_{1-4}$-alkylamino, $C_{2-5}$-alkanoylamino or $C_{2-5}$-alkoxycarbonyl groups or two $R^1$ substituents on the same nitrogen atom may together form a straight or branched chain alkylene radical containing from 4 to 6 carbon atoms in the chain which is unsubstituted or substituted as defined for alkyl radicals represented by $R^1$ (e g. 1-methoxymethyltetramethylene) and pharmaceutically acceptable salts thereof.

Preferably X represents the carbonyl group or a group of formula $>C=NOR^1$ as hereinbefore defined.

The group Ar is preferably substituted in the 3 and-/or 5 position with an electron-withdrawing group for example a cyano, nitro, trifluoromethyl, carbamoyl, carboxy, $C_{2-5}$-alkanoyl, $C_{2-5}$-alkoxycarbonyl or $C_{1-4}$-alkylsulphonyl group or a fluorine, chlorine or bromine atom, and optionally further substituted with halogen atom(s), $C_{1-4}$-alkyl or $C_{6-12}$-aryl (e.g. phenyl) group(s), or the group Ar may be substituted with halogen atom(s), $C_{1-4}$-alkyl or $C_{6-12}$-aryl (e.g. phenyl) group(s) or with substituents which together form a fused ring, for example a 2-naphthyl group.

The group Ar may represent, for example, the phenyl, 4-chlorophenyl, 3-trifluoromethylphenyl, 3-nitrophenyl, 3,4-dichlorophenyl or 2-naphthyl group.

The presence of a hydroxy group on the ring creates an asymmetry in the molecule which, in association with the adjacent asymmetric carbon atom, leads to 4 stereoisomers which, optionally, can be separated into 2 racemic pairs. The racemic pair and its enantiomers of the general formula (II) in which R, Ar and Y are as hereinbefore defined, i.e. the compounds in which the hydroxy group is in the trans position relative to the group —CSNHR are preferred.

Furthermore, in certain cases the substituents R and $R^1$ contribute to stereoisomerism. All such forms are embraced by the present invention.

Particular compounds of the present invention are as follows:-

A  (±)-N-methyl-2-oxo-1-phenylcyclohexanecarbothioamide
B  (±)-trans-N-methyl-2-hydroxy-1-phenylcyclohexanecarbothioamide
C  (±)-anti-N-methyl-2-hydroxyimino-1-phenylcyclohexanecarbothioamide
D  (±)-anti-N-methyl-2-methoxyimino-1-phenylcyclohexanecarbothioamide
E  (±)-N-methyl-2-oxo-1-(4-chlorophenyl)cyclohexanecarbothioamide
F  (±)-N-methyl-2-oxo-1-(3-trifluoromethylphenyl)-cyclohexanecarbothioamide
G  (±)-anti-N-methyl-2-benzyloxyimino-1-(3,4-dichlorophenyl)cyclohexanecarbothioamide
H  (±)-anti-N-methyl-2-(4-fluorobenzyloxyimino)-1-phenylcyclohexanecarbothioamide,
I  (±)-N-methyl-2-oxo-1-(2-naphthyl)cyclohexanecarbothioamide
J  (±)-N-methyl-2-oxo-1-(3,4-dichlorophenyl)cyclohexanecarbothioamide
K  (±)-N-methyl-2-oxo-1-(3-nitrophenyl)-cyclohexanecarbothioamide as well as their enantiomeric and diastereoisomeric and syn forms, where they exist.

The letters A to K are allocated to the compounds for easy reference later in the specification, e.g. in the Table and in the Examples.

The compounds have valuable pharmacological properties, in particular properties which are indicative of utility in the treatment and/or prophylaxis of disorders associated with:-

(1) vascular smooth muscle contraction including hypertension and other cardiovascular disorders such as congestive heart failure, and conditions associated with tissue ischaemia such as angina, peripheral vascular disease and cerebrovascular disease;

(2) respiratory smooth muscle contraction including reversible airways obstruction and asthma;

(3) contraction of smooth muscle of gastro-intestinal tract, urinary bladder and uterus, including peptic ulcers, irritable bowel syndrome and diverticular disease; irritable bladder syndrome; and premature labour.

The compounds also have utility in the inhibition of head hair loss associated with male pattern baldness, by topical application.

For example, compounds of general formula (I) were submitted to:-

Vaso-relaxant Activity Tests

The test methods used were adapted from those described by Winslow et al [Eur.J.Pharmacol., 131, 219–228 (1986)] and Karaki [J.Pharmacol. Methods, 18, 1–21 (1987)] for differentiating vaso-relaxant activity.

Test A: Activity against contractions induced by low $K^+$ concentrations in the isolated rat aorta Thoracic aorta was removed from rats and transverse strips, denuded of endothelium, were suspended in a bath containing Krebs solution. The tension was recorded and a contraction induced by addition of 20 mM K+ (potassium ion) to the bathing solution. The test compound was added to the bath as a solution in increasing cumulative concentration. The concentration in the bathing solution of the test compound which reduced the K+-induced contraction by 90% was determined and expressed in μM as the effective concentration (EC$_{90}$), given in Table I.

Test B : Activity against contractions induced by high K+ concentrations in isolated rat aorta The test method was as in Test A except that contractions were induced by addition of 60 mM K+ to the bathing solution. The cumulative addition of solutions of the test compound was conducted and the concentration in the bath reducing the K+-induced contraction by 90% was greater than 30 μM for Compounds C, D, E, F, I, J and K, and much greater than 30 μM for Compound A.

TABLE I

| Compound | Activity Test A EC$_{90}$ μM |
| --- | --- |
| A | 29 |
| C | >30 |
| D | 20 |
| E | 12 |
| F | 0.9 |
| H | 0.6 |
| I | 2.0 |
| J | 0.4 |
| K | 0.7 |

The compounds of general formula (I) can be prepared by the application or adaptation of known methods, for example as hereinafter identified. By the term "known methods" as used in this specification is meant methods hereto fore used or described in the literature.

According to a feature of the present invention, the compounds of general formula (I) wherein X represents the carbonyl group or a group of formula >C=NOR$^1$ or >C=NN(R$^1$)$_2$ wherein R$^1$ is as hereinbefore defined may be prepared by the reaction of a compound of general formula (III) wherein X' represents the carbonyl group or a group of formula >C=NOR$^1$ or >C=NN(R$^1$)$_2$ as hereinbefore defined and Ar and Y are as hereinbefore defined with an isothiocyanate of the general formula:

$$R\text{—}N\text{=}C\text{=}S \qquad \text{(IV)}$$

wherein R represents a straight- or branched-chain alkyl radical containing 1 to 4 carbon atoms.

The reaction is generally carried out in an anhydrous inert organic solvent such as tetrahydrofuran, dimethyl formamide or hexamethylphosphoramide, or a mixture of these solvents, at a temperature from −80° C. to +50° C., in the presence of an organic base such as potassium tert.-butoxide or an organo-lithium derivative such as butyllithium, or of sodium hydride.

According to a feature of the present invention, the compounds of general formula (I) wherein X represents the hydroxymethylene group may be prepared by the reduction of a compound of general formula (I) wherein X represents the carbonyl group.

The reduction is generally carried out in an inert organic solvent such as methanol or dimethylsulphoxide, or a mixture of these solvents at a temperature from −20° C. to +50° C., using an alkali metal borohydride, e.g. sodium borohydride.

According to a feature of the present invention, the compounds of general formula (I) wherein X represents a group of the formula: >C=NOR$^1$, >C=NN(R$^1$)$_2$ or >C=NN(R$^1$)CON(R$^1$)$_2$ as hereinbefore defined may be prepared by the reaction of a compound of general formula (I) wherein X represents the carbonyl group with a compound of general formula:

| | |
| --- | --- |
| NH$_2$OR$^1$ | (Va) |
| NH$_2$N(R$^1$)$_2$ | (Vb) or |
| NH$_2$N(R$^1$)CON(R$^1$)$_2$ | (Vc) | wherein R$^1$ is as hereinbefore defined or with an acid addition salt (preferably the hydrochloride) thereof.

The reaction is generally carried out in the presence of an inorganic base, e.g. sodium carbonate or sodium acetate in an inert organic solvent, e.g. ethanol, or an organic base, e.g. pyridine, which may serve as the solvent, in an inert organic solvent at a temperature from 0° C. to 120° C.

A stereoselective synthesis may be performed in which a mixture of enantiomers of general formula (III) wherein X' represents the carbonyl group is reacted with a chiral auxiliary agent, e.g. (S)-1-amino-2-methoxymethylpyrrolidine, before being reacted with a compound of general formula (IV) as hereinbefore described followed by the removal of the chiral auxiliary agent.

According to a feature of the invention, the thioformamide derivatives of general formula (I) wherein R represents the methyl radical and X represents the carbonyl group or a group of the formula >C=NOR$^1$ or >C=NN(R$^1$)$_2$ as hereinbefore defined may be prepared by the process which comprises reacting methylamine with a dithioester of the general formula (VI) wherein the symbols Ar, X' and Y are as hereinbefore defined, and R' represents a straight- or branched-chain alkyl radical containing 1 to 4 carbon atoms, or a benzyl or carboxymethyl radical.

In general, the reaction is carried out with an excess of methylamine, without a solvent or in an organic solvent such as an aromatic hydrocarbon, an ether or an alcohol of low molecular weight, or a mixture of these solvents, at a temperature from 20° to 130° C., optionally under pressure.

It is particularly advantageous for the thiol formed during the reaction to be fixed in the form of a heavy metal salt using a thiol acceptor such as mercuric chloride.

The dithioester of general formula (VI) can be obtained by the following methods:

(1) By reaction of a strong base with a compound of the general formula (III) (wherein X', Ar, and Y are as hereinbefore defined), followed by reacting the resulting product with carbon disulphide and then with a compound of the general formula:

$$R'\text{—}Z \qquad \text{(VII)}$$

wherein R' is as hereinbefore defined, and Z represents a halogen atom, preferably a chlorine, bromine or iodine atom, or a reactive ester radical, preferably a mesyloxy or tosyloxy radical.

The reaction is generally carried out in an ether such as tetrahydrofuran, to which hexamethylphosphoramide has generally been added, at a temperature between −20° and +50° C.

It is particularly advantageous to employ potassium tert.-butoxide as the strong base. Alternatively the organo-lithium derivatives described above may be employed.

It will be understood that it may be desirable to change one or more of the substituents at an appropriate stage during the synthesis of the compounds of the invention, for example, the compounds of general formula (I) wherein Ar represents a phenyl group substituted by a carbamoyl group may be alternatively prepared from the corresponding compounds of general formula (I) wherein Ar represents a phenyl group substituted by a cyano group by the application or adaptation of known methods for such conversion.

The thioformamide derivatives of general formula (I) obtained by the aforedescribed processes can be purified by the usual physical methods, in particular crystallisation and chromatography, especially to resolve mixtures of enantiomers using a chiral column.

Compounds of general formulae (III) and (V) may be prepared by known methods.

By the term "pharmaceutically acceptable salts" as used in this specification is meant salts the anions or cations of which are relatively innocuous to the animal organism when used in therapeutic doses so that the beneficial pharmaceutical properties of the parent compounds of general formula (I) capable of forming salts are not vitiated by side-effects ascribable to those anions or cations.

As well as being useful in themselves as active compounds, acid addition salts of the compounds of general formula (I) capable of forming such salts are useful for the purposes of purification of the parent compounds of general formula (I), for example by exploitation of the solubility differences between the salts and the parent compounds, by techniques well known to those skilled in art. The parent compounds of general formula (I) can be regenerated from their acid addition salts by known methods, for example by treatment with an alkali, e.g. aqueous sodium bicarbonate solution or aqueous ammonia solution.

Suitable acid addition salts for use in pharmaceuticals may be selected from salts derived from inorganic acids, for example hydrochlorides, hydrobromides, phosphates, sulphates and nitrates, and organic acids, for example oxalates, lactates, tartrates, acetates, salicylates, citrates, propionates, succinates, fumarates, maleates, methylene-bis-$\beta$-hydroxynaphthoates, gentisates and di-p-toluoyltartrates As well as being useful in themselves as active compounds, salts of the compounds of general formula (I) capable of forming salts with bases are useful for the purposes of purification of the parent compounds of general formula (I), for example by exploitation of the solubility differences between the salts and the parent compounds, by techniques well known to those skilled in the art.

Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmethylamine) salts.

The following Examples illustrate the preparation of compounds according to the present invention.

Unless stated otherwise, all the spectra were recorded at 200 MHz in deuterochloroform; the chemical shifts are expressed in ppm relative to the tetramethylsilane signal. The abbreviations used in the following text are as follows:

s = singlet
d = doublet
t = triplet
m = multiplet
c = unresolved bands
dd = doublet of doublets
dt = doublet of triplets
ddd = doublet of doublets of doublets
dddd = doublet of doublets of doublets of doublets

EXAMPLE 1

Compounds A, E and F

A solution of ($\pm$)-2-phenylcyclohexanone (3.0 g, 17.2 mmol) at −15° C. in tetrahydrofuran (40 ml) was treated with potassium t.-butoxide (1.9 g, 17.2 mmol) during 2 minutes. After 15 minutes at −15° C., a solution of methyl isothiocyanate (1.38 g, 19 mmol) in tetrahydrofuran (20 ml) was added dropwise during 2 minutes and the resulting solution was stirred for 3 hours at 0° C. Water (200 ml) followed by chloroform (200 ml) were added to the reaction mixture and the aqueous layer was extracted with chloroform (200 ml). The combined organic extracts were washed with brine (150 ml) then dried over sodium sulphate. Concentration in vacuo (30° C.; 14 mm Hg) afforded a crude oil (4.2 g) which was purified by flash chromatography over silica gel eluting with a 1:1 mixture of diethyl ether and hexane to give ($\pm$)-N-methyl-2-oxo-1-phenylcyclohexanecarbothioamide (1.5 g, 6.1 mmol) m.p. 86° C. N.M.R. (CDCl$_3$) 1.62-2.05 (c, 4H), 2.42-2.56 (m, 2H), 2.64-2.84 (ddd, 1H), 3.0-3.18 (c, 4H), 7.23-7.45 (c, 5H) 8.72-9.06 (broad singlet, 1H). Found C, 68.3; H, 7.2; N, 5.8; S, 13 0%, C$_{14}$H$_{17}$NOS requires C, 68.0; H, 6.9; N, 5.7; S, 13.0%.

By proceeding in a similar manner to that hereinbefore described but replacing the ($\pm$)-2-phenylcyclohexanone by the appropriately substituted ($\pm$)-2-phenylcyclohexanone, there were prepared:-

($\pm$)-N-methyl-2-oxo-1-(4-chlorophenyl)cyclohexanecarbothioamide, a colourless solid, melting point 125°-127° C., after being purified by flash chromatography on silica gel eluting with toluene/ethyl acetate: 100/0.25, followed by trituration with ether;

($\pm$)-N-methyl-2-oxo-1-(3-trifluoromethylphenyl)-cyclohexanecarbothioamide, a pale yellow solid, melting point 118°-120° C., after purification by flash chromatography on silica gel eluting with ether/pentane: 1/1, followed by trituration with pentane. The reaction was carried out at −40° C. After addition of methyl isothiocyanate the temperature was allowed to rise slowly to 20° C. and maintained at that level for 24 hours.

EXAMPLE 2

Compound B

A solution of ($\pm$)-N-methyl-2-oxo-1-phenylcyclohexanecarbothioamide (0.44 g, 1.78 mmol) in a mixture of dimethylsulphoxide (6 ml) and methanol (6 ml) at −10° C. was treated with sodium borohydride (0.07 g, 1.8 mmol) in one portion. After 2 hours at −10° C. the reaction mixture was warmed at 20° C. and maintained at this temperature for 1.5 hours. The mixture was treated with water (20 ml) then extracted with ethyl acetate (2×50 ml). The combined extracts were washed with brine then dried over sodium sulphate and concentrated in vacuo to give a crude oil (0.58 g) which was recrystallised from a 3:1 mixture of hexane and ethyl acetate to give (±)-trans-N-methyl-2-hydroxy-1-phenylcyclohexanecarbothioamide (0.2 g, 8.0 mmol) m.p. 118°-119° C. N.M.R. (CDCl$_3$) 1.2-1.78 (m, 6H), 1.80-2.0 (m, 1H), 2.14-2.30 (dt, 1H), 2.30-2.46 (ddd, 1H), 3.0-3.08 (d, 3H), 4.76-4.94 (m, 1H), 7.0-7.24 (broad singlet, 1H), 7.24-7.48 (m, 3H), 7.64-7.84 (m, 2H). Found: C, 67.9; H, 7.6; N, 5.5; S, 12.9%: C$_{14}$H$_{19}$NOS requires C, 67.4; H, 7.7; N, 5.6; S, 12.9%.

EXAMPLE 3

Compound C

A suspension of (±)-N-methyl-2-oxo-1-phenylcyclohexanecarbothioamide (0.6 g, 2.4 mmol) in pyridine (6 ml) at 20° C. was treated with hydroxylamine hydrochloride (0.34 g, 4.9 mmol) and stirred for 18 hours. The resulting solution was poured into water (50 ml) and extracted with ethyl acetate (3×50 ml). The combined organic extracts were washed successively with water (15 ml) and brine (15 ml) then dried over sodium sulphate. Concentration in vacuo (30° C.; 14 mm Hg) afforded a crude oil which was recrystallised from isopropanol (6 ml) to give (±)-anti-N-methyl-2-hydroxyimino-1-phenylcyclohexanecarbothioamide (0.27 g, 1.03 mmol) m.p. 182°-184° C. N.M.R. (CDCl$_3$) 1.28-1.84 (c, 4H); 2.20-2.40 (m, 1H); 2.42-2.58 (m, 1H); 2.78-2.86 (dt, 1H); 3.04-3.26 (c, 4H); 7.20-7.58 (m, 6H); 8.40 (s, 1H); Found: C, 64.4; H, 7.0; N, 10.6; S, 12.% C$_{14}$H$_{18}$N$_2$OS requires C, 64.1; H, 6.9; N, 10.7; S, 12.2%.

EXAMPLE 4

Compound D

A suspension of (±)-N-methyl-2-oxo-1-phenylcyclohexanethioamide (0.5 g, 2 mmol), in pyridine (5 ml) at 20° C. was treated with O-methylhydroxylamine hydrochloride (0.34 g, 4 mmol).

After stirring for 48 hours at 20° C. the solution was poured into water (50 ml) and the mixture was then extracted with ethyl acetate (4×50 ml). The combined organic extracts were washed with water (20 ml) then dried over sodium sulphate. Concentration in vacuo (25° C./14 mmHg) afforded a crude oil (0.67 g) which was recrystallised from isopropanol to give (±)-N-anti-N-methyl-2-methoxyimino-1-phenylcyclohexanecarbothioamide (0.2 g, 0.7 mml), melting point 79°-80° C. N.M.R. (CDCl$_3$) 1.34-1.72 (c, 3H), 2.72-2.92 (m, 1H), 2.16-2.36 (m, 1H), 2.56-2.96 (m, 3H), 3.10-3.16 (d, 3H), 3.86 (s, 3H), 7.20-7.46 (c, 5H), 8.10-8.44 (broad singlet, 1H). Found C, 65.2; H, 7.6; N, 10.2; S, 11.7% : C$_{15}$H$_{20}$N$_2$OS. Requires C, 65.2; H, 7.3; N, 10.1; S, 11.6%.

EXAMPLE 5

Compounds G and H

A stirred suspension of (±)-N-methyl-2-oxo-1-(3,4-dichlorophenyl)cyclohexanecarbothioamide (2.75 g) and benzyloxyamine hydrochloride (1.46 g) in ethanol (25 ml) and pyridine (5 ml) was refluxed for 24 hours. The mixture was evaporated, the residue dissolved in chloroform (75 ml), washed with water (3×50 ml), dried over magnesium sulphate, and evaporated. The residual oil was purified by flash chromatography on silica, eluting with toluene to give (±)-anti-N-methyl-2-benzyloxyimino-1-(3,4-dichlorophenyl)cyclohexanecarbothioamide (2.8 g), yellow crystals, m.p. 103°-105° C.

By proceeding in a similar manner to that hereinbefore described but replacing the (±)-N-methyl-2-oxo-1-(3,4-dichlorophenyl) cyclohexanecarbothioamide by (±)-N-methyl-2-oxo-1-phenylcyclohexanecarbothioamide and benzyloxyamine hydrochloride by 4-fluorobenzyloxyamine hydrochloride, there was prepared:-
(±)-anti-N-methyl-2-(4-fluorobenzyloxyimino)-1-phenylcyclohexanecarbothioamide, m.p. 65° C.

EXAMPLE 6

Compounds I and J

By proceeding in a similar manner to that hereinbefore described in Example 1, there were prepared:-
(±)-N-methyl-2-oxo-1-(2-naphthyl)cyclohexanecarbothioamide, a colorless crystalline solid, m.p. 126°-127° C., after purification by flash chromatography over silica gel eluting with toluene/ethyl acetate: 99/1 and triturating with ether;
(±)-N-methyl-2-oxo-1-(3,4-dichlorophenyl)cyclohexanecarbothioamide, a colourless crystalline solid, m.p. 146°-147° C., after purification by flash chromatography on silica gel eluting with toluene and triturating with ether.

EXAMPLE 7

Compound K

A solution of (±)-2-(3-nitrophenyl)cyclohexanone (1 g, 4.5 mmol) and methyl isothiocyanate at 20° C. in tetrahydrofuran (15 ml) was treated with sodium hydride (120 mg, 5 mmol) added in one portion. The mixture was stirred vigorously. After 13 minutes, water (20 ml) was added and the mixture extracted with ethyl acetate (2×20ml). The combined organic extracts were dried over magnesium sulphate. Concentration in vacuo (30° C., 14 mmHg) afforded a crude oil (0.95 g) which was purified by flash chromatography over silica gel, eluting with toluene/acetone: 96/4 and trituration with equal portions of hexane and diethyl ether to give (±)-N-methyl-2-oxo-1-(3-nitrophenyl)-cyclohexanecarbothioamide (0.1 g, 0.35mmol) m.p. 128°-132° C.

The present invention includes within its scope pharmaceutical compositions which comprise a compound of general formula (I) or a pharmaceutically acceptable salt thereof, in association with a pharmaceutically acceptable carrier or coating. In clinical practice the compounds of the present invention may be administered rectally, but are preferably administered parenterally, by inhalation if appropriate, or, more preferably, orally.

Solid compositions for oral administration include compressed tablets, pills, powders and granules. In such solid compositions, one or more of the active compounds is, or are, admixed with at least one inert diluent such as starch, sucrose or lactose. The compositions may also comprise, as is normal practice, additional substances other than inert diluents, e.g. lubricating agents, such as magnesium stearate.

Liquid compositions for oral administration include pharmaceutically acceptable emulsions, solutions, suspensions, syrups and elixirs containing inert diluents commonly used in the art such as water and liquid paraffin. Besides inert diluents such compositions may comprise adjuvants, such as wetting, and suspending agents, and sweetening, flavouring, perfuming and preserving agents. The compositions according to the invention for oral administration also include capsules of absorbable material such as gelatin, containing one or more of the active substances with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. The compositions may also contain adjuvants such as stabilising, preserving, wetting, emulsifying and dispersing agents. They may be sterilized by, for example, filtration through a bacteria-retaining filter, by incorporation in the compositions of sterilizing agents, by irradiation or by heating. They may also be manufactured in the form of sterile solid compositions, which can be dissolved in sterile water or some other sterile injectable medium immediately before use.

Compositions for inhalation may be sterile aqueous solutions which are then nebulised or dry powders formulated in accordance with known methods.

Solid compositions for rectal administration include suppositories formulated in accordance with known methods and containing one or more of the compounds of formula (I) or a pharmaceutically acceptable salt thereof.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from 0.001 to 50 mg/kg body weight per day by oral administration. By inhalation, either as a nebulised solution or as a formulated dry powder, the preferred daily dosage is from 0.001 to 5 mg/kg body weight.

The compounds may also be applied topically for inhibition of head hair loss associated with male pattern baldness the preferred daily dosage being from 0.1 to 10 mg/kg body weight applied, for example, in 5 ml portions two or three times per day.

The following Example illustrates pharmaceutical compositions according to the present invention.

COMPOSITION EXAMPLE

No. 2 size gelatin capsules each containing:-(±)-N-methyl-2-oxo-1-phenylcyclohexane-

| carbothioamide | 20 mg |
| lactose | 100 mg |
| starch | 60 mg |
| dextrin | 40 mg |
| magnesium stearate | 1 mg | were prepared in accordance with the usual procedure.

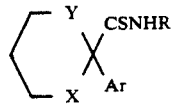

-continued

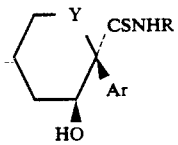

II

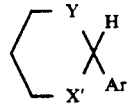

III

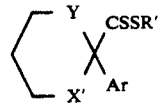

VI

We claim:
1. A thioformamide derivative of the formula:

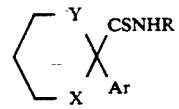

wherein R represents a straight- or branched-chain alkyl radical containing from 1 to 4 carbon atoms, Ar represents an unsubstituted phenyl group, or a phenyl group substituted in the 3- and/or 5-position with an electron-withdrawing group selected from the group consisting of a cyano, nitro, trifluoromethyl, carbamoyl, carboxy, $C_{2-5}$-alkanoyl, $C_{2-5}$-alkoxycarbonyl or $C_{1-4}$-alkylsulphonyl group or a fluorine, chlorine or bromine atom and optionally further substituted with halogen, $C_{1-4}$ alkyl or $C_{6-12}$ aryl or the group Ar is substituted with at least one halogen atom, at least one $C_{1-4}$ alkyl or $C_{6-12}$ aryl group or Ar represents a naphthyl, Y represents an ethylene or methylene radical or a valency bond, and X represents a carbonyl or hydroxymethylene group or a group of the formula: $>C=NOR^1$ or $>=NN(R^1)_2$ in which the symbols $R^1$, which may be the same or different, each represents the hydrogen atom or a straight- or branched- chain alkyl radical containing from 1 to 4 carbon atoms which is unsubstituted or substituted by one or more substituents selected from $C_{2-4}$-alkenyl, carboxy, $C_{2-5}$-alkoxycarbonyl, hydroxy, $C_{1-4}$-alkoxy, carbamoyl, unsubstituted or substituted by one or two $C_{1-4}$-alkyl groups, amino, $C_{1-4}$-alkylamino and di-$C_{1-4}$-alkylamino groups or represents a benzyl, phenethyl, 1-naphthyl-methyl or 2-naphthylmethyl radical each of which may be substituted on the ring by at least one halogen atom or hydroxy, $C_{1-4}$-alkyl, $C_{1-4}$ alkoxy, alkoxy being unsubstituted or substituted as defined for alkyl groups represented by $R^1$, cyano, nitro, trifluoromethyl, carboxy, $C_{1-4}$-alkylamino, $C_{2-5}$-alkanoylamino or $C_{2-5}$-alkoxycarbonyl groups, or a pharmaceutically acceptable salt thereof.

2. A compound according to claim 1 wherein X represents the carbonyl group or a group of formula $>C=NOR^1$ as defined in claim 1.

3. A compound according to claim 1 wherein Y represents a methylene radical.

4. A compound according to claim 1 wherein Ar represents the phenyl, 4-chlorophenyl, 3-trifluoromethylphenyl, 3-nitrophenyl, 3,4-dichlorophenyl or 2-naphthyl group.

5. A compound according to claim 1 of the formula:

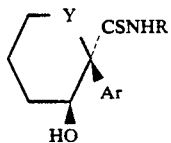

(II)

(wherein Y, R and Ar are as defined in claim 1) in which the hydroxy group is in the trans position relative to the group —CSNHR.

6. A compound according to claim 1, wherein the group Ar is optionally further substituted with at least one halogen atom, at least one $C_{1-4}$-alkyl or phenyl group or Ar represents naphthyl.

7. A compound according to claim 1 which is ($\pm$) -N-methyl-2-oxo-1-phenylcyclohexanecarbothioamide, ($\pm$)-trans-N-methyl-2-hydroxy-1-phenylcyclohexanecarbothioamide, ($\pm$)-anti-N-methyl-2-hydroxyimino-1-phenylcyclohexanecarbothioamide, ($\pm$)-anti-N-methyl-2-methoxyimino-1-phenylcyclohexanecarbothioamide ($\pm$)-N-methyl-2-oxo-1-(4-chlorophenyl)cyclohexanecarbothioamide, ($\pm$)-N-methyl-2-oxo-1-(3-trifluoromethylphenyl)cyclohexanecarbothioamide, ($\pm$)-anti-N-methyl-2-benzyloxyimino-1-(3,4-dichlorophenyl)cyclohexanecarbothioamide, ($\pm$)-anti-N-methyl-2-(4-fluorobenzyloxyimino)-1-phenylcyclohexanecarbothioamide, ($\pm$)-N-methyl-2-oxo-1-(2-naphthyl)cyclohexane-carbothioamide, ($\pm$)-N-methyl-2-oxo-1-(3,4-dichlorophenyl)cyclohexanecarbothioamide or ($\pm$)-N-methyl-2-oxo-1-(3-nitrophenyl)-cyclohexanecarbothioamide, or a pharmaceutically acceptable salt thereof.

8. A pharmaceutical composition useful in the treatment and/or prophylaxis of a disorder associated with vascular smooth muscle contraction, tissue ischaemia, respiratory smooth muscle contraction and contraction of smooth muscle of the gastro-intestinal tract, urinary bladder or uterus, which comprises an amount effective to combat said disorder of a thioformamide derivative of formula (I) as defined in claim 1 or a pharmaceutically acceptable salt thereof in association with a pharmaceutically acceptable carrier or coating.

* * * * *